(12) United States Patent
Knauper

(10) Patent No.: US 7,843,328 B2
(45) Date of Patent: Nov. 30, 2010

(54) MEDICAL DEVICE WITH SELECTABLE STATUS MONITORING MODES

(75) Inventor: Christopher A. Knauper, O'Fallon, MO (US)

(73) Assignee: Covidien AG (CH)

( * ) Notice: Subject to any disclaimer, the term of this patent is extended or adjusted under 35 U.S.C. 154(b) by 1129 days.

(21) Appl. No.: 11/284,575

(22) Filed: Nov. 22, 2005

(65) Prior Publication Data

US 2007/0118186 A1   May 24, 2007

(51) Int. Cl.
G08B 1/08 (2006.01)
(52) U.S. Cl. .............. 340/539.12; 340/539.11; 340/573.1; 340/540; 607/60
(58) Field of Classification Search ........... 340/539.12, 340/539.11, 539.13, 573.1, 10.1, 540, 539.19, 340/539.1, 10.51, 825.36, 825.49, 825.69, 340/825.72; 607/60, 59; 128/903, 904
See application file for complete search history.

(56) References Cited

U.S. PATENT DOCUMENTS

| | | | |
|---|---|---|---|
| 4,817,044 A | 3/1989 | Ogren | |
| 5,338,157 A | 8/1994 | Blomquist | |
| 5,789,675 A * | 8/1998 | Blaine et al. | 73/290 R |
| 6,168,563 B1 | 1/2001 | Brown | |
| 6,363,282 B1 | 3/2002 | Nichols et al. | |
| 6,418,346 B1 | 7/2002 | Nelson et al. | |
| 6,497,655 B1 | 12/2002 | Linberg et al. | |
| 6,544,228 B1 | 4/2003 | Heitmeier | |
| 6,940,403 B2 * | 9/2005 | Kail, IV | 340/539.12 |
| 7,009,511 B2 * | 3/2006 | Mazar et al. | 340/531 |
| 7,154,398 B2 * | 12/2006 | Chen et al. | 340/573.1 |
| 2002/0111542 A1 | 8/2002 | Warkentin et al. | |
| 2003/0046439 A1 | 3/2003 | Manke et al. | |
| 2004/0077995 A1 | 4/2004 | Ferek-Petric et al. | |
| 2004/0128161 A1 | 7/2004 | Mazar et al. | |
| 2004/0167587 A1 | 8/2004 | Thompson | |

FOREIGN PATENT DOCUMENTS

| | | |
|---|---|---|
| GB | 2386957 | 10/2003 |
| WO | WO 2004/030757 | 4/2004 |
| WO | WO 2004/060155 | 7/2004 |
| WO | WO 2005/053786 | 6/2005 |

* cited by examiner

*Primary Examiner*—Anh V La
(74) *Attorney, Agent, or Firm*—Edward S. Jarmolowicz, Esq.

(57) ABSTRACT

A medical device including a control circuit and a plurality of selectable communication modes. The control circuit controls the medical device and generates a signal representative of a characteristic of the medical device. A selected one of the plurality of selectable communication modes communicates the signal generated by the control circuit at a configurable messaging rate.

32 Claims, 3 Drawing Sheets

US 7,843,328 B2

MEDICAL DEVICE WITH SELECTABLE STATUS MONITORING MODES

FIELD OF THE INVENTION

The present invention generally relates to communicating the status of a medical device to a monitoring device at another location. More particularly, the invention relates to a medical device communicating its status according to a mode selected from a plurality of status communication modes.

BACKGROUND OF THE INVENTION

Communicating with a medical device over a network is known in the art. These medical devices have a fixed communication mode specific to the environment in which they are used.

For example, because of the Health Insurance Portability and Accountability Act (HIPAA), medical devices deployed in some environments do not communicate at all. In intensive care units (ICU), it is beneficial to report the status of the medical device to a central unit frequently, while using as little of the network and monitoring station resources as possible. To achieve these goals, medical devices for use in ICU environments often use a communications mode that requires the medical device to report its status at a preset interval. In other environments, it may not be necessary to receive status updates as often as in the ICU environment. In this case, it often requires less of the network and monitoring station resources to use a mode wherein a medical device only reports its status when queried. This may also be a preferred mode if the user is not concerned with network and monitoring station resource consumption.

Currently, medical devices are designed for use in only one of the above environments.

SUMMARY OF THE INVENTION

A single medical device that can be used in multiple environments or systems within a facility would save the cost of buying a separate unit for use in each environment. It is therefore desirable to have a medical device that will work within multiple systems having different communications modes. More specifically, it is desirable to have a medical device with multiple, selectable communications modes.

In accordance with one aspect of the invention, a medical device is provided. The medical device includes a control circuit and a plurality of selectable communication modes. The control circuit controls the medical device and generates a signal representative of a characteristic of the medical device. A selected one of the plurality of selectable communication modes communicates the signal generated by the control circuit.

In accordance with another aspect of the invention, a method is provided for communicating a status of a medical device. Power is supplied to the medical device. One of a plurality of selectable communications modes is selected. The selected communications mode is loaded to an operating communications mode, and the status of the medical device is transmitted in accordance with the operating communications mode.

In accordance with another aspect of the invention, a medical device status monitoring system is provided. The monitoring system includes at least one medical device, a server, and a communication medium. The medical device has a plurality of selectable communications modes and a communications device for sending status messages and receiving status queries. The server has a communications device for sending the status queries and receiving the status messages. The communication medium transfers the status messages from the at least one medical device to the server and the status queries from the server to the medical device.

In accordance with another aspect of the invention, an enteral feeding pump is provided. The feeding pump includes a control circuit and a plurality of selectable communication modes. The control circuit controls the operation of the pump and generates a signal representative of an operational characteristic of the pump. A selected one of the plurality of selectable communication modes communicates the signal generated by the control circuit.

Alternatively, the invention may comprise various other methods and apparatuses.

Other objects and features will be in part apparent and in part pointed out hereinafter.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

Corresponding reference characters indicate corresponding parts throughout the drawings.

DETAILED DESCRIPTION OF THE INVENTION

In one embodiment, the invention is a medical device having selectable multiple communication modes and a communications device. For example, the communication modes include off, periodic, and controlled. In the off mode, the medical device will not communicate any information through a communications device. In the periodic mode, the medical device sends status messages at a predetermined interval via the communications device. In the controlled mode, the medical device sends status messages only when queried by a server receiving the status messages. The modes may be selected by user input or by signals received via the communications device.

Figure 1:
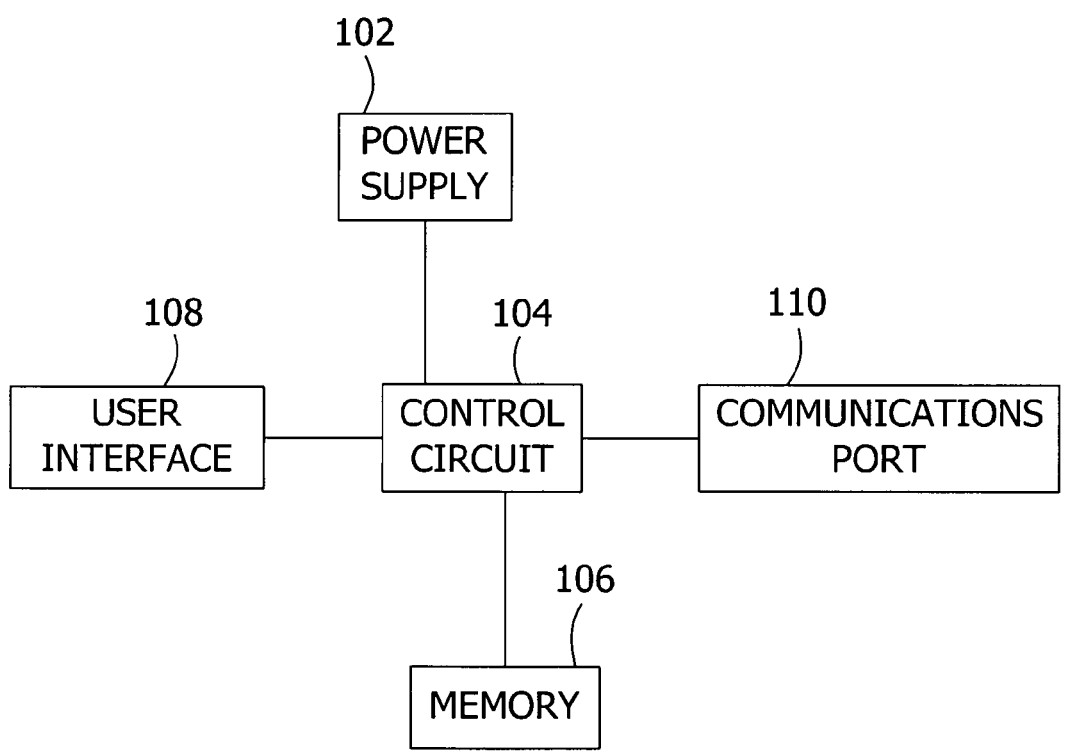
FIG. 1 is a system for monitoring status of at least one medical device according to one embodiment of the invention.

Referring now to FIG. 1, a medical device employing the invention is shown. A power supply 102 supplies power to a control circuit 104. The power supply 102 may be an integral part of the medical device (e.g. batteries) or it may be external to the medical device (e.g. 120V AC wall outlet and any transformers or rectifiers). The control circuit 104 initializes and reads in information from memory 106. The memory 106 contains data relating to settings of the device and a selected one of a plurality of communication modes. It is contemplated that the memory 106 may be an integral portion of the control circuit 104. A user interface 108 displays data relating to the medical device and a user can enter data to cause the control circuit 104 to perform functions of the medical device. The control circuit 104 determines a characteristic of the medical device such as its operating status or a parameter derived during the performance of the medical device's functions and transmits that characteristic through communications port 110 according to the selected one of the plurality of communication modes. The selected communication mode may be changed by user input through user interface 108 or by messages received through communications port 110.

Referring now to FIG. 1, a status monitoring system according to another embodiment of the invention is shown. The system 100 includes at least one medical device 102, a server 110, and a communication medium 108. The medical device 102 has a communications port 104 for sending status messages and receiving status queries. The medical device 102 also has a user interface 106 for displaying medical device data and receiving user input. The medical device 102 has a plurality of communication modes. The communications medium 108 connects the server 110 to the communications port 104 of the medical device 102. The communications medium 108 may be wired or wireless. Examples of communications mediums include a serial network, a TCP/IP network, a LAN, a WAN, the Internet, and IEEE 802.11.

Figure 2:
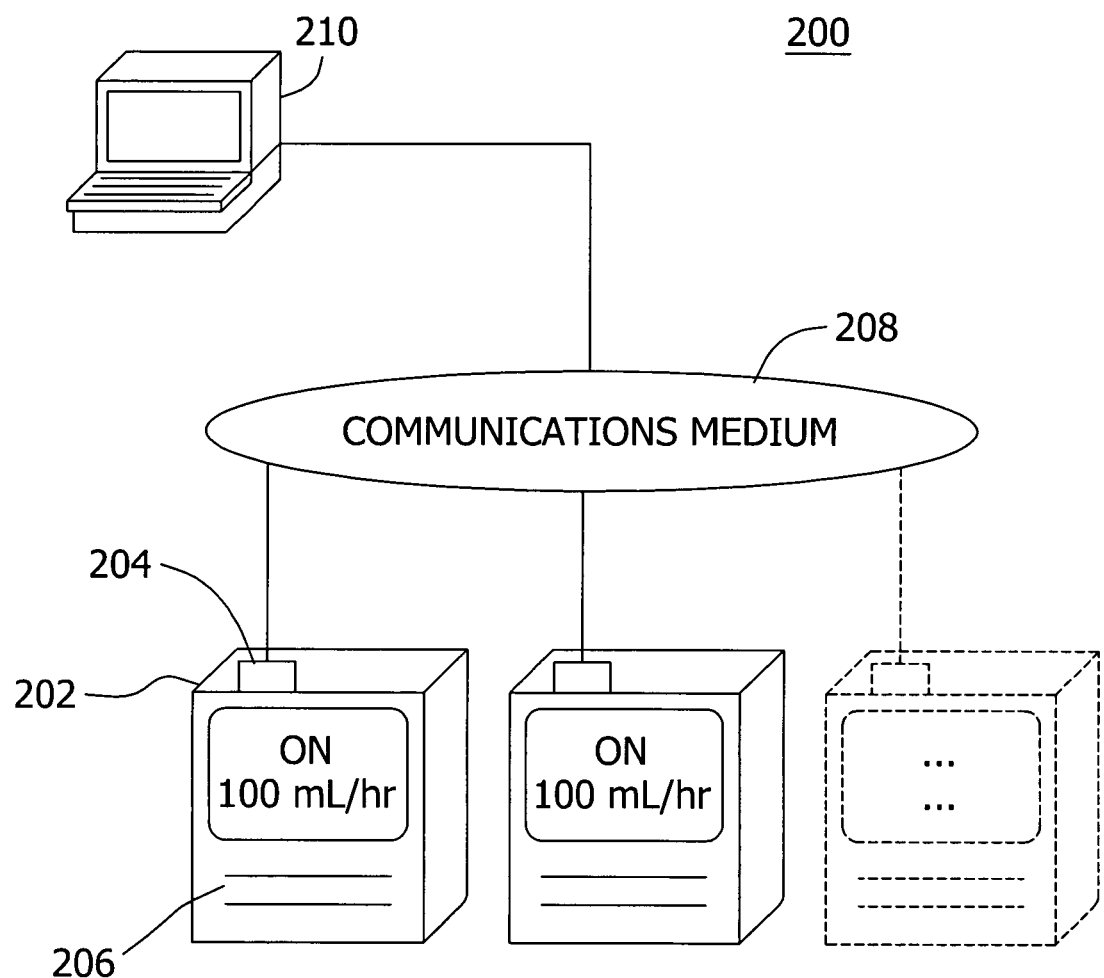
FIG. 2 is a system for monitoring status of at least one medical device according to an alternative embodiment of the invention.

In FIG. 2, the medical device 202 has multiple communication modes for communicating a characteristic of the medical device 202 that may be utilized by this single system 200. By way of example and not limitation, the medical device 202 may have 3 communication modes including off, periodic, and controlled. In the off mode, the medical device 202 does not send any status messages via communications port 204 nor respond to any signals received via the communication port 204 such that a corresponding configurable messaging rate in this mode is zero. In the periodic mode, the medical device 202 sends status messages to the server 210 through the communications medium 208 via the communications port 204 at a preset interval such that the corresponding configurable messaging rate in the periodic mode is the preset interval. In controlled mode, the server 210 sends a status query to the communications port 204 via the communications medium 208. In response to receiving the status query, the medical device 202 sends a status message to the server 210 such that the corresponding configurable messaging rate in this communication mode is the query interval. The medical device 202 switches communications modes in response to user input received through the user interface 206 or signals received through the communications port 204 so that the single system 200 may dynamically select from multiple communication modes. In one embodiment, it should also be noted that the system 200 communicates in one selected communication mode even though the medical device 202 is capable of multiple communication modes.

Figure 3:
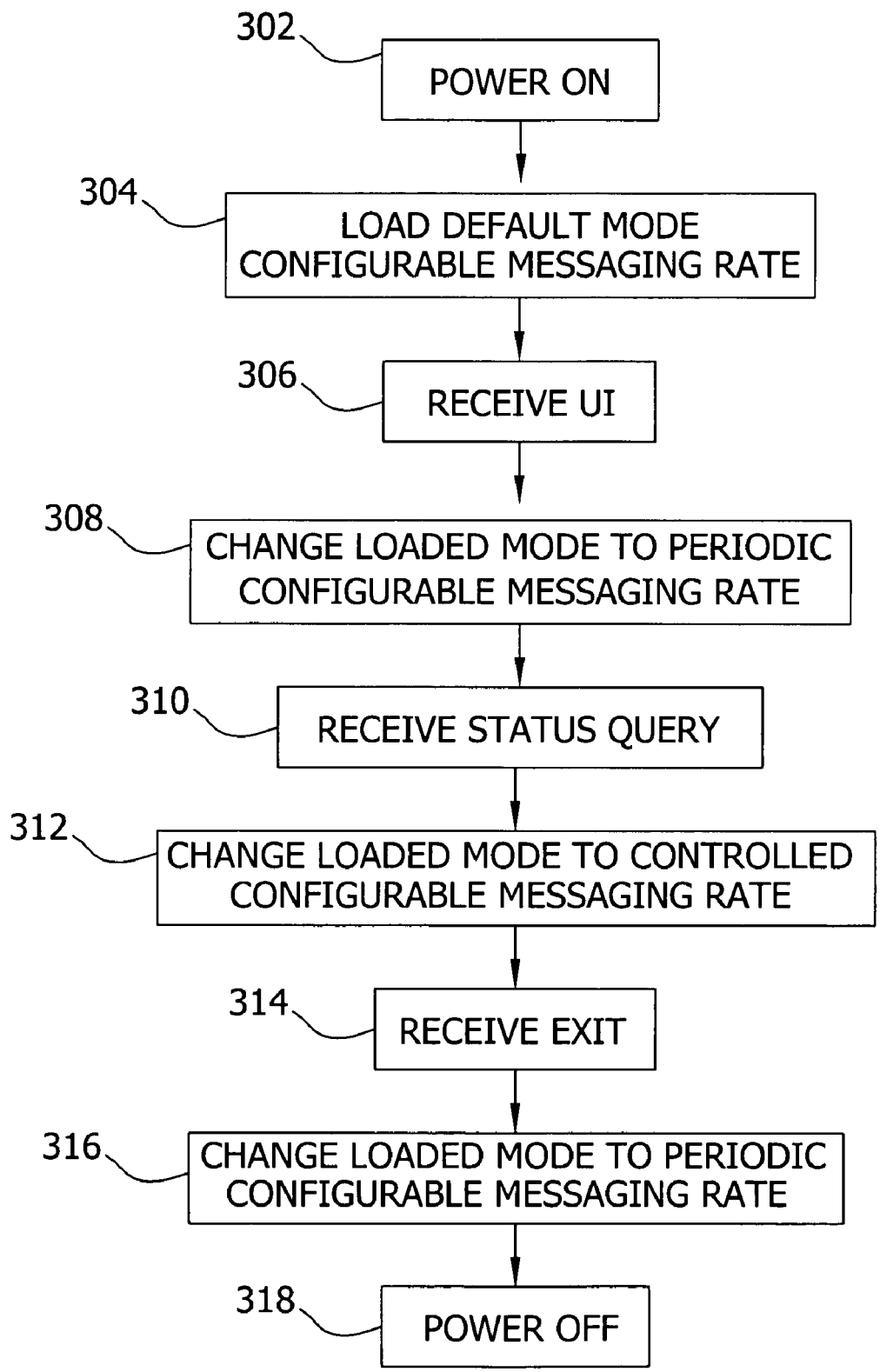
FIG. 3 is a flow chart illustrating a method for switching between multiple communication modes according to one embodiment of the invention.

Referring now to FIG. 3, a method of communicating a status of a medical device is shown according to anther embodiment of the invention. At step 302, a medical device is powered on. During the medical device's initialization routine, it loads a default communication mode at step 304. In this example, the default communication mode is off. The medical device does not transmit status messages in this communication mode. At step 306, a user inputs data into the medical device through the medical device's user interface. The data changes the loaded communication mode to periodic and the medical device begins transmitting status messages accordingly. At step 310, the medical device receives a status query from a server through its communications port. In response to the status query, at step 312, the medical device changes its loaded communication mode to controlled. The medical device then transmits status messages according to the loaded communication mode (e.g. transmits a status message when it receives a status query from the server). At step 314, the medical device receives an exit message (or other suitable control command) through its communications port from the server. In response, the medical device changes its loaded mode to periodic at step 316. At step 318, the device is powered off. In this embodiment, since the last communication mode used was something other than off, the medical device will start up with periodic as its default mode. One skilled in the art however, should recognize that the default communication mode stored in memory could be the last communication mode loaded before the medical device was powered off, or always be a particular communication mode, whatever that mode may be.

In another embodiment of the invention, a medical device with flash memory is provided. A default communication mode is stored in the flash memory. When the device is turned on, the default communication mode is loaded into main memory and the copy in main memory is an operating communication mode. The default communication mode can only be changed via the user interface of the device. The operating communication mode, however, can be changed by data received through the communication port.

It should be noted that status messages as referred to above may take different forms. In one communications protocol, status messages may always be the same length and contain the same information. In another communications protocol, status messages may differ according to various operating modes of the medical device. For example, in one operating mode of a medical pump, the data is continuous flow parameters whereas in another operating mode, the data includes bolus parameters. In another communications protocol, status messages are one length and contain one set of data when the medical device is operating properly, and status messages are actually error messages of a different length and containing a different set of data when the medical device is not operating properly. Status messages preferably identify the medical device to the system. This can be accomplished by including the serial number of the medical device in each message. Likewise, a status query in a system with multiple medical devices can identify which device it is intended for by including the device's serial number in each query.

Examples of medical devices that may advantageously employ aspects of the invention are pulse meters, pulse oximeters, blood pressure meters, glucose monitors, drug pumps, and thermometers.

One example of a medical device implementing aspects of the invention is an enteral feeding pump, which has a serial communication port, a user interface, and 3 communication modes. The communication modes are off, periodic, and controlled. In the off mode, the pump will not send any communication through the serial port no matter what data is received via the serial port. In the periodic mode, the pump sends a message indicating the status of the pump every five seconds. In the controlled mode, the pump sends a message only when requested. In operation, when the pump is turned on, the default communication mode is off. The user can change the default communication mode to periodic via the user interface. Once the pump is in periodic mode, receiving an 'r' via the serial port will cause the pump to switch to controlled mode. Receiving an 'x' will cause the pump to switch back to periodic mode. Status messages are sent when the pump is operating properly and contain data relating to statistics of the pump operation. When the pump is not functioning properly, it reverts to periodic mode and sends an error message. The error message is shorter and contains the error data being displayed on the pump's user interface. Appendix A describes exemplary message formats used by the enteral feeding pump. These message formats are applicable to other medical devices implementing the invention. Appendix B further describes exemplary communication modes used by the enteral feeding pump.

Having described the invention in detail, it will be apparent that modifications and variations are possible without departing from the scope of the invention defined in the appended claims.

The order of execution or performance of the methods illustrated and described herein is not essential, unless otherwise specified. That is, it is contemplated by the inventors that elements of the methods may be performed in any order, unless otherwise specified, and that the methods may include more or less elements than those disclosed herein. For example, it is contemplated that executing or performing a particular element before, contemporaneously with, or after another element is within the scope of the various embodiments of the invention.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description and shown in the accompanying drawings shall be interpreted as illustrative and not in a limiting sense.

Appendix A

Messages
  Communication Settings
  Compatible Serial Port settings are Baud Rate: 9600, Data Bits: 8, Parity: N, Stop Bits: 1.
  Basic Message Format All messages have the following format:
  pumpTBD|########|XXXX|YYYY|****|???. . . ???|CC||CRLF where
  | are message element separators
  pump is the message header
  TBD is the message type code, either "STS" or "ERR"
  ######## is the 7 digit pump Serial Number in hexidecimal (4 bytes)
  XXXX is the Software Major Version in hexidecimal (2 bytes)
  YYYY is the Software Minor Version in hexidecimal (2 bytes)
  **** is the Message Status Flag in hexidecimal (2 bytes)
  ???. . . ??? are the Message Data elements in hexidecimal separated by "|". Content and size depend on the type of message.
  CC is the CRC check of the Serial #, Software Version, Message Status Flag, and Message Data portions (1 byte)
  || is the message end signal
  CRLF are the carriage return and line feed characters for easier display.
  These are the last characters in every message.

Message Types

Status Messages
Message Type: Status
Type Code: STS
Frequency (Default Reporting Mode): Every 5 seconds
Description: Status Messages contain information on the user's settings and present operation of the unit. They are overridden and replaced by Error messages, when applicable.

Error Messages
Message Type: Error
Type Code: ERR
Format: See Description
Frequency (Default Reporting Mode): Every 5 seconds when asserted
Description: Error Messages contain information on the Error currently visible on the pump display. When asserted, these messages override and replace Status messages.

Field Descriptions

Status Flag (****)

The Flag portion is 2 bytes in length and communicates up to 16 On/Off items through status bits. These are:

| Flag | Bit | True (1) | False (0) |
| --- | --- | --- | --- |
| Running | 0x0001 | Pump is in Running Mode (Running Screen is displayed) | Pump is NOT in Running Mode (Running Screen is NOT displayed) |
| Bolus Mode | 0x0002 | Bolus Mode selected | Continuous Mode selected |
| Bolus Break Time | 0x0004 | Waiting for Next Bolus to start | NOT Waiting for Next Bolus to start |
| Super Bolus | 0x0008 | Super Bolus selected | Super Bolus NOT selected |
| Feeding Complete | 0x0010 | VTBD is nonzero AND required VTBD has been reached | VTBD is 0 OR required VTBD has NOT been reached. |
| Auto Resume | 0x0020 | Auto Resume is set | Auto Resume NOT set |
| Feed Set loaded | 0x0040 | Feed Only set loaded | Other or No Set loaded |
| Flush Set loaded | 0x0080 | Feed/Flush set loaded | Other or No Set loaded |
| Feed Totalizer Cleared | 0x0100 | User pressed "Clear Volume" button since last message sent by pump. | User powered up or message was sent by pump more recently than "Clear Volume" pressed. |
| Power Source | 0x0200 | AC Power available | Battery Power only |
| Battery Charging | 0x0400 | Battery is currently charging | Battery is NOT being charged |
| EZ Mode | 0x0800 | EZ-pump mode is set | Normal Mode |
| Settings Locked | 0x1000 | Settings are Locked | Settings are NOT Locked |
| Screen Locked | 0x2000 | Run Mode Screen Lock function Enabled | Run Mode Screen Lock function Disabled |

-continued

| Flag | Bit | True (1) | False (0) |
|---|---|---|---|
| Controlled Report Mode | 0x4000 | Controlled Reporting Mode | Default Reporting Mode |
| (Available) | 0x8000 | UNDEFINED | UNDEFINED |

Message Data for Status Messages (??? ... ???)

The data portion of the status message consists of 20 bytes of settings/status data. The parameters displayed depend on whether Continuous or Bolus Mode is set (available through the Status Flag). Data items are separated by "|" All of these numbers are represented as 2 or 4 byte integers in hexidecimal form:

| Continuous Mode | Bolus Mode | Bytes |
|---|---|---|
| Flush Totalizer | Flush Totalizer | 4 |
| Flush VTBD | Flush VTBD | 2 |
| Flush Interval | Flush Interval | 2 |
| Feed Totalizer | Bolus Totalizer | 4 |
| Feed Rate | Bolus Rate | 2 |
| Feed VTBD | Bolus VTBD | 2 |
| Feed VTBD remaining | Bolus Interval | 2 |
| N/A (Always 0) | Number of Boluses | 2 |

Message Data for Error Messages (??? ... ???)

The data portion of the error message consists of 3 bytes of error information. It consists of a 2 byte Error screen index (Error ID) in hexidecimal, a Data item separator "|", and then a 1 byte System Error number in hexidecimal, if applicable. If not applicable, this number is 0.

| Error Screen | Error ID | System Error Code |
|---|---|---|
| System Error | 102 | (0-255) |
| Pump Set Dislodged | 106 | 0 |
| Battery Low | 150 | 0 |
| Feed Error | 120 | 0 |
| Flush Error | 121 | 0 |
| Flow Error | 122 | 0 |
| Hold Error | 101 | 0 |
| Rotor Error | 111 | 0 |

CRC (CC)

For both types of messages, the following fields are used in the computation of the CRC (field separators are not included in the computation). The CRC appears as a 1 byte hexidecimal number near the end of each message:

Serial Number, Software Major Version, Software Minor Version, Message Status Flag, Message Data Each byte of each element MSB to LSB is run through the following algorithms with each result building on the last byte's computation. Below, CRCShift is the result of the previous byte's computation. A zero is used as the initial condition for CRCShift:

C Implementation:

```
/*----------------------------------------------------------------
---*/
    /* Given an initial CRC as CRCShift (which could be 00), compute
the 8 bit CRC of input byte and return CRC. */
unsigned char GetCRC(unsigned char CRCShift, unsigned char InputByte)
{
    int i;
    unsigned NextBit, Stage8th, XORStage8th, XORMask;
    for (i=0; i<=7; i++)
    {
        NextBit = GetBit(InputByte,i);
        Stage8th = GetBit(CRCShift,0);
        XORStage8th = NextBit ^ Stage8th;
        XORMask = 0;
        XORMask = SetBit(XORMask, 7, XORStage8th);
        XORMask = SetBit(XORMask, 3, XORStage8th);
        XORMask = SetBit(XORMask, 2, XORStage8th);
        CRCShift = CRCShift >> 1;
        CRCShift = CRCShift & 0x7F; /* zero the 1 shifted in
        from the
left*/
        CRCShift = CRCShift ^ (unsigned char)XORMask;
    }
    return CRCShift;
}
/*----------------------------------------------------------------
-----------------------------*/
/* Return value of bit n in a word (rightmost bit is bit number
zero). */
unsigned GetBit(unsigned word, int n)
{
    return (word >> n) & 01;
}
/*----------------------------------------------------------------
-----------------------------*/
/* Return value with bit n set to v (0 or 1) (rightmost bit is bit
number zero). */
unsigned SetBit(unsigned word, int n, unsigned v)
{
    if (v != 0)
        return word | (01 << n);      /* turn on
                                         the bit. */
    else
        return word & ~(01 << n);     /* turn off
                                         the bit. */
}
```

Visual Basic Implementation:

```
/*----------------------------------------------------------------
-----------------------------*/
Public Function fnGetCRC(CRCShift As Byte, InputByte As
Byte) As Byte
Dim i As Integer
Dim NextBit, Stage8th, temp As Integer
Dim XORStage8th As Integer
Dim XORMask As Integer
For i = 0 To 7
    NextBit = fnGetBit(CInt(InputByte), i)
    Stage8th = fnGetBit(CInt(CRCShift), 0)
    XORStage8th = NextBit Xor Stage8th
    XORMask = 0
    XORMask = fnSetBit(XORMask, 7, XORStage8th)
    XORMask = fnSetBit(XORMask, 3, XORStage8th)
    XORMask = fnSetBit(XORMask, 2, XORStage8th)
    CRCShift = Int(CRCShift / 2)
    CRCShift = CRCShift And &H7F
    CRCShift = CRCShift Xor CByte(XORMask)
Next i
fnGetCRC = CRCShift
End Function
```

```
/*----------------------------------------------------------------
----------------------------*/
Public Function fnSetBit(word As Integer, n As Integer, v
    As Integer) As Integer
Dim testword As Integer
Dim Bits(8), j As Integer
testword = word
For j = 7 To 0 Step -1
    Bits(j) = 0
    If testword >= 2 ^ j Then
        testword = testword - 2 ^ j
        Bits(j) = 1
    End If
Next j
If v <> 0 Then ' equals 1, set bit
    If Bits(n) <> 1 Then
        Bits(n) = 1
        word = word + 2 ^ n
    End If
Else 'equals 0, unset bit
    If Bits(n) <> 0 Then
        Bits(n) = 0
        word = word - 2 ^ n
    End If
End If
fnSetBit = word
End Function
/*----------------------------------------------------------------
----------------------------*/
Public Function fnGetBit(word As Integer, n As Integer) As Integer
Dim Bits(8), j As Integer
'word is the source
'n is the bit index
For j = 7 To 0 Step -1
    Bits(j) = 0
    If word >= 2 ^ j Then
        word = word - 2 ^ j
        Bits(j) = 1
    End If
Next j
fnGetBit = Bits(n)
End Function
```

Translation Methodology

To isolate discrete messages, it should be verified that all messages either start with "pumpSTS" and have a total length of 87 (carriage return and line feed characters are located at the 86$^{th}$ and 87$^{th}$ locations in the message, respectively) or "pumpERR" and have a total length of 47 (carriage return and line feed characters are located at the 46$^{th}$ and 47$^{th}$ locations in the message, respectively). Length can be verified by making sure the last and second to last characters are line feed and carriage return characters.

This description of the form of the message should allow custom programs to isolate discrete messages from the pump.

Communication Verification Techniques

The program decoding the message should verify the message is free of communication errors by using one of the following two suggested techniques:

Method 1 (Basic):

Verify the characters in every field other than the header and message type fields ("pumpSTS" or "pumpERR") is made up of only the number characters 0-9 and the upper case letters A-F.

Method 2 (Advanced):

Compute the CRC using the algorithm described above and verify it matches the value of the CRC at the end of the message.

Sample Messages

Status Message—Continuous Mode pumpSTS
|00000038|0003|000A|0801|0000152C|012C|0002|
000007D0|0190|0BB8|03E8|0000|F5||

| Message Portion | Converted Value | Meaning |
|---|---|---|
| pumpSTS | pumpSTS | Message Type is Status |
| 0x00000038 | 56 | Serial Number C0000056 |
| 0x0003 | 3 | Software Major Version 3 (Software v3.10) |
| 0x000A | 10 | Software Minor Version 10 (Software v3.10) |
| 0x0401 | Running, EZ Status Bits are ON | Running Continuous EZ mode |
| 0x0000152C | 5420 ml | Flush Totalizer |
| 0x012C | 300 ml | Flush VTBD |
| 0x0002 | 2 hrs | Flush Interval |
| 0x000007D0 | 2000 ml | Feed Totalizer |
| 0x0190 | 400 ml/hr | Feed Rate |
| 0x0BB8 | 3000 ml | Feed VTBD |
| 0x03E8 | 1000 ml | Feed VTBD remaining |
| 0x0000 | 0 | (This field always 0) |
| 0xF5 | 245 | CRC is 245 |

Status Message—Intermittent Mode pumpSTS|00000038|0003|000A|0602|0000152C|012C|
0002|00000002|0190|0BB8|0008|0003|3E||

| Message Portion | Converted Value | Meaning |
|---|---|---|
| pumpSTS | PumpSTS | Message Type is Status |
| 0x00000038 | 56 | Serial Number C0000056 |
| 0x0003 | 3 | Software Major Version 3 (Software v3.10) |
| 0x000A | 10 | Software Minor Version 10 (Software v3.10) |
| 0x0302 | Bolus Mode, AC Power, Battery Charging Status Bits are ON | Intermittent Mode, AC Power, Battery is Charging, not Running |
| 0x0000152C | 5420 ml | Flush Totalizer |
| 0x012C | 300 ml | Flush VTBD |
| 0x0002 | 2 hrs | Flush Interval |
| 0x00000002 | 2 Boluses | Bolus Totalizer |
| 0x0190 | 400 ml/hr | Bolus Rate |
| 0x0BB8 | 3000 ml | Bolus VTBD |
| 0x0008 | 8 hrs | Bolus Interval |
| 0x0003 | 3 Boluses | Number of Boluses |
| 0x3E | 62 | CRC is 62 |

Error Message—System Error #33 pumpERR|00000038|0003|000A|0002|0066|21|72||

| Message Portion | Converted Value | Meaning |
|---|---|---|
| pumpERR | pumpERR | Message Type is Error |
| 0x00000038 | 56 | Serial Number C0000056 |
| 0x0003 | 3 | Software Major Version 3 (Software v3.10) |
| 0x000A | 10 | Software Minor Version 10 (Software v3.10) |
| 0x0002 | Bolus Mode Status Bit is ON | Intermittent Mode, not Running |
| 0x0066 | 102 | System Error, Screen # |
| 0x21 | 33 | System Error, Error # |
| 0x72 | 114 | CRC is 114 |

Error Message—Flow Error pumpERR|00000038|0003|000A|0000|007A|00|A9||

| Message Portion | Converted Value | Meaning |
| --- | --- | --- |
| pumpERR | pumpERR | Message Type is Error |
| 0x00000038 | 56 | Serial Number C0000056 |
| 0x0003 | 3 | Software Major Version 3 (Software v3.10) |
| 0x000A | 10 | Software Minor Version 10 (Software v3.10) |
| 0x0000 | Bolus Mode Status Bit NOT ON | Continuous Mode |
| 0x007A | 122 | Flow Error, Screen # |
| 0x00 | 0 | System Error, Error # (not applicable) |
| 0xA9 | 169 | CRC is 169 |

Appendix B

Pump Reporting Modes

The pump will have three reporting modes in the normal mode of operation: Off, Default, and Controlled. In all cases, incoming serial data will be processed by pump as processing time permits via the main control loop.

Off

This is the default setting of the pump upon construction of the unit. The pump will not send any messages out over the serial port nor will it recognize any incoming commands. The Communication icon indicating serial communication is not shown in the display. If the Communication option in the Biotech Options menu is turned on, the pump will enter Default Reporting Mode. The status of the Communication option is saved in the Flash and will persist when the pump is rebooted.

Default Reporting Mode

In this mode, the pump automatically sends a Status OR Error message out over the Serial Port every 5 seconds. The pump defaults to this mode upon every powerup assuming the Communication option has been turned on. While in this mode, the Communication icon will be visible near the battery icon except in the Power Down, System Error, and Low Battery screens. If the "EZ pump Mode" is also on, the EZ and Communication icons will toggle as they occupy the same space on the screen. The pump will clear the special Feed Totalizer Cleared flag every time a message is sent. If an "r" is received while in this mode, it will switch into the Controlled Reporting Mode and send the first message as described in Controlled Reporting Mode. All other data received over the serial port in Default Reporting Mode is ignored.

Controlled Reporting Mode

In this mode, the pump sends a Status OR Error message out over the Serial Port only when requested by the host computer. When the pump receives an "r" while in this mode, it sends a single message out over the port and blinks the Communication icon for 20 seconds. If the EZ pump mode is also on, the EZ and Communication icons will toggle. The pump will clear the special Feed Totalizer Cleared flag every time a message is sent. Upon receiving an "x", the pump will switch back to Default Reporting Mode. All other data received over the serial port in Controlled Reporting Mode is ignored. No more than one message will be sent every 5 seconds regardless of the number of requests. Size of the request buffer is 1.

What is claimed is:

1. A medical device comprising:
    a control circuit for controlling the medical device, said control circuit generating a signal representative of a characteristic of the medical device; and
    a plurality of switchable and selectable communication modes of the control circuit for communicating the signal generated by the control circuit at a user-configurable messaging rate, said user-configurable messaging rate having a single value selectable from zero, a preset interval, and a query interval.

2. The medical device of claim 1, wherein the selectable communication modes comprise at least the following:
    a first communications mode enabling the device to periodically report a status message at the preset interval;
    a second communications mode enabling the device to report a status message in response to a query at the query interval; and
    a third communications mode disabling the device from reporting a status message when the user-configurable messaging rate is zero.

3. The medical device of claim 2, further comprising a user interface responsive to user input for selecting one of the first, second, or third communications modes.

4. The medical device of claim 1, wherein the selectable communications modes include a default communications mode.

5. The medical device of claim 4, wherein the control circuit is configured to disable the device from reporting a status message when in the default communications mode.

6. The medical device of claim 4 wherein the control circuit is configured to enable the device to periodically report a status message when in the default communications mode.

7. The medical device of claim 1, wherein the control circuit is responsive to user input for selecting among the plurality of selectable communications modes.

8. The medical device of claim 7, wherein the user input comprises a status query.

9. The medical device of claim 1, further comprising a user interface responsive to user input for selecting one of the selectable communications modes.

10. The medical device of claim 1, further comprising a serial port coupled to the control circuit for communicating the signal generated by the control circuit according to a selected one of the communications modes and for receiving a selection of one of the communications modes.

11. The medical device of claim 1, further comprising a wireless transmitter coupled to the control circuit for communicating the signal generated by the control circuit according to a selected one of the communications modes and for receiving a selection of one of the communications modes.

12. A method of communicating a status of a medical device comprising:
    supplying power to the medical device;
    selecting one of a plurality of switchable and selectable communications modes of said medical device, said selecting comprising receiving a single specification of a configurable messaging rate having a value chosen from zero, a preset interval, and a query interval;
    loading the selected communications mode to an operating communications mode; and
    transmitting the status of the medical device in accordance with said operating communications mode at the specified configurable messaging rate.

13. The method of claim 12, wherein transmitting the status of the medical device comprises sending a message indicating the status at a preset interval.

14. The method of claim 12, wherein transmitting the status of the medical device comprises sending a message indicating the status in response to a status query.

15. The method of claim 12, wherein selecting one of the plurality of selectable communications modes of said medical device comprises receiving a communications signal and altering the operating communications mode of said medical device in response to receiving the communications signal.

16. The method of claim 15, wherein said communications signal is a status query.

17. The method of claim 12, wherein selecting the communications mode comprises receiving user input via a user interface for selecting one of the plurality of selectable communications modes.

18. The method of claim 12, wherein the selectable communications modes comprise at least the following:
 a first communications mode enabling the device to periodically report a status message;
 a second communications mode enabling the device to report a status message in response to a query; and
 a third communications mode disabling the device from reporting a status message.

19. The method of claim 18, wherein selecting one of the plurality of selectable communications modes comprises selecting one of the first, second, or third communications modes as a default communications mode.

20. The method of claim 12, wherein transmitting the status of the medical device comprises communicating the status via a serial port.

21. The method of claim 12, wherein transmitting the status of the medical device comprises communication the status via wireless transmission.

22. A medical device status monitoring system comprising:
 at least one medical device having a first communications device for sending status messages at a configurable messaging rate and receiving status queries, said configurable messaging rate having a value selectable from zero, a preset interval, and a query interval, said at least one medical device having a plurality of switchable and selectable communications modes;
 a server having a second communications device for receiving said status messages and for sending said status queries; and
 a communication medium for transferring said status messages from the at least one medical device to the server, and for transferring said status queries from the server to the at least one medical device.

23. The medical device status monitoring system of claim 22, wherein the selectable communications modes of the medical device comprise at least the following:
 a first communications mode enabling the device to periodically report a status message;
 a second communications mode enabling the device to report a status message in response to a query; and
 a third communications mode disabling the device from reporting a status message.

24. The medical device status monitoring system of claim 23, wherein the medical device comprises a user interface for selecting one of the first, second, or third communications modes.

25. The medical device status monitoring system of claim 22, wherein the selectable communications modes of the medical device include a default communications mode.

26. The medical device status monitoring system of claim 25, wherein the medical device is configured to be disabled from reporting a status message when in the default communications mode.

27. The medical device status monitoring system of claim 25, wherein the medical device is configured to be enabled to periodically report a status message when in the default communications mode.

28. The medical device status monitoring system of claim 22, wherein the medical device is responsive to user input for selecting among the plurality of selectable communications modes.

29. The medical device status monitoring system of claim 28, wherein the user input to the medical device comprises the status query sent by the server.

30. An enteral feeding pump comprising:
 a control circuit for controlling operation of the pump, said control circuit generating a signal representative of an operational characteristic of the pump; and
 a plurality of switchable and selectable communication modes for communicating the signal generated by the control circuit at a configurable messaging rate, said configurable messaging rate having a single value selectable from zero, a preset interval, and a query interval.

31. The pump of claim 30, wherein the selectable communications modes comprise at least the following:
 a first communications mode enabling the device to periodically report a status message;
 a second communications mode enabling the device to report a status message;
 and a third communications mode disabling the device from reporting a status message.

32. The pump of claim 30, wherein the operational characteristic includes at least one of the following: running status; bolus mode status; bolus break time status; super bolus status; feeding complete status; auto resume status; feed set load status; flush set status; feed totalizer clear status; power source status; battery charging status; normal mode status; lock status; and communications mode status.

* * * * *